US005891705A

United States Patent [19]
Budowsky et al.

[11] Patent Number: 5,891,705
[45] Date of Patent: Apr. 6, 1999

[54] METHOD FOR INACTIVATING A VIRUS

[75] Inventors: Edward I. Budowsky, Brookline; Samuel K. Ackerman, Weston, both of Mass.

[73] Assignee: Pentose Pharmaceuticals, Inc., Cambridge, Mass.

[21] Appl. No.: 835,446

[22] Filed: Apr. 8, 1997

[51] Int. Cl.[6] .............................. C12N 7/06; C12N 7/04; C12N 7/00
[52] U.S. Cl. ...................... 435/238; 435/235.1; 435/236
[58] Field of Search ................................ 435/235.1, 236, 435/238

[56] References Cited

U.S. PATENT DOCUMENTS

| 3,492,289 | 1/1970 | Symm et al. | 260/239 |
| 4,841,023 | 6/1989 | Horowitz . | |
| 5,009,951 | 4/1991 | Bass et al. . | |
| 5,055,485 | 10/1991 | Geacintov et al. . | |
| 5,120,649 | 6/1992 | Horowitz et al. | 435/173 |
| 5,232,844 | 8/1993 | Horowitz et al. | 435/173.1 |
| 5,374,424 | 12/1994 | Kelsey et al. | 424/202.1 |

FOREIGN PATENT DOCUMENTS

| 0612532 A2 | 8/1994 | European Pat. Off. . |
| 101400 | 4/1992 | Romania . |
| 1768636 A1 | 10/1992 | U.S.S.R. . |
| 594771 A1 | 7/1993 | U.S.S.R. . |
| WO 92/03157 | 3/1992 | WIPO . |
| WO 92/18161 | 10/1992 | WIPO . |
| WO 96/39818 | 12/1996 | WIPO . |

OTHER PUBLICATIONS

Bahnemann, Hans G., Vaccine, vol. 8, "Inactivation of Viral Antigens for Vaccine Preparation with Particular Reference to the Application of Binary Ethylenimine," pp. 299–303 (Aug. 1990).
Budowsky, Edward I. et al., Vaccine Research, vol. 5, No. 1, "Principles of Selective Inactivation of the Viral Genome: Dependence of the Rate of Viral RNA Modification on the Number of Protonizable Groups in Ethyleneimine Oligomers," pp. 29–39 (1996).
Budowsky, Edward I. et al., Vaccine, vol. 9, "Principles of Selective Inactivation of Viral Genome. V. Rational Selection of Conditions for Inactivation of the Viral Suspension Infectivity to a Given Extent by the Action of β–propiolactone," pp. 319–325 (May 91).
Dermer, O. C. et al., Academic Press, Ethylenimine and Other Aziridines, "Ring–Destroying Reactions of Aziridines," pp. 248–285 (1969).
Earley, J.E., et al., Contribution from the Metcalf Chemical Laboratories of Brown University, vol. 80, "Reactions of Ethylenimines. IX. The Mechanisms of Ring Openings of Ethylenimines in Acidic Aqueous Solutions," pp. 3458–3462 (Jan. 11, 1958).

Kostyanovskii, R.G., et al., Bulletin of the Academy of Sciences of the USSR, vol. 37, No. 11, Part 2, "Oligomers of Aziridines and N–β–Aziridinoethylamides," pp. 2315–2325 (1989).
Kochetkov, N.K. et al., Organic Chemistry of Nucleic Acids, Part A, Plenum Press, "Structure of the Nucleic Acids," pp. 48–55 (1971).
Race, Esther et al., Vaccine, vol. 13, No. 1, "An Experimental Chemically Inactivated HIV–1 Vaccines Induces Antibodies that Neutralize Homologous and Heterologous Viruses," pp. 54–60 (1995).
Bahnemann, H.G., "Inactivation of Viruses in Serum with Binary Ethyleneimine", Journal of Clinical Microbiology, vol. 3, No. 2, pp. 209–210 (1975).
Budowsky et al., "Inactivation of the phage MS2 infectivity by the action of ethyleneimines," Biorg. Khim. 11:989–991 (1985) (in Russian). English Translation provided, 3 pages.
King, "Evaluation of Different Methods of Inactivation of Newcastle Disease Virus and Avian Influenza Virus in Egg Fluids and Serum," Avian Diseases 35:505–514 (1991).
Prodouz et al., "Inhibition of Merocyainine 540–mediated Photosensitization of Platelets and Viruses," Transfusion 31:415–422 (1991).
Tanirbergenov, T.B. et al., "Regularities of mutagenic and toxic effects of ethyleneimine and its oligomers. A comparative study in the automated system SOS–chromotest and in standard bacterial test systems," Genetika 24:763 (1988) (in Russian). English translation provided, 5 pages.
Van Etten, R.L. and Dolhum, J.J., "Effects of HydrogenBond Formation by Phenols on the Conformational Equilibrium of trans–1,2–Dimethyl–3–isopropylaziridine," J. Org. Chem. 33:3904–3907 (1968).
Wagner et al., "Approaches to the Reduction of Viral Infectivity in Cellular Blood Components and Single Donor Plasma," Transfusion Med. Rev. V:18–32 (1991).
Budowsky, U.S. Patent Application Serial No.: 08/521,245, filed Aug. 29, 1995, entitled: "Methods and Compositions for the Selective Modification of Nucleic Acids".
Budowsky, U.S. Patent Application Serial No.: 08/705,045, filed Aug. 29, 1996, entitled: "Methods and Compositions for the Selective Modification of Nucleic Acids".
Twomey, et al. Structure and immunogenicity of experimental foot–and–mouth disease and poliomyelitis vaccines, Vaccine, vol. 13, No. 16, pp. 1603–1610, 1995.

Primary Examiner—Lynette F. Smith
Assistant Examiner—Brenda G. Brumback
Attorney, Agent, or Firm—Clark & Elbing LLP

[57] ABSTRACT

The present invention concerns a method for inactivating a virus for use in e.g. a vaccine, by treating the virus with an ethyleneimine at a pH of less than 7.0, and methods of treatment with the inactivated virus.

8 Claims, No Drawings

METHOD FOR INACTIVATING A VIRUS

BACKGROUND OF THE INVENTION

The invention relates to a method of preparing viruses for use in vaccines.

Inactivation of a virus can alter viral antigens, reducing the safety or efficacy of the vaccine. Ideally, the conditions and agent(s) for viral inactivation would selectively and irreversibly affect the viral genome.

Ethyleneimine monomer (EI) or binary ethyleneimine (BEI) are reagents used to modify nucleic acids preferentially at N-7, N-3, and N-1 of purines and to a lesser extent N-3 of pyrimidines. Alkylating agents enhance the opening of an imidazole ring of N-7 alkylated purines (e.g., guanine), thereby arresting replication. EI alkylates guanosine to form N-7 (aminoethyl)guanosine which has a higher imidazole ring opening rate than does N-7 (alkylguanosine). EI also modifies non-genomic components of the viron or nonviral biomolecules.

One undesirable side-effect of this nonspecific reactivity is the disruption of viral particles which reduces immunogenicity. Chemical modification of even a single amino acid can significantly change the resistance of protein toward proteinases and may reduce stability of vaccine during storage due to proteolysis of modified viral proteins. Preferential inactivation of protective epitopes can contribute to an imbalanced immune response and to potentiation of disease during subsequent infection. Modification of capsid components can inhibit the intracellular processing of viral proteins which are necessary for presentation of epitopes to T-cells. Third, modification of amino acid residues of viral proteins reduces viral antigenicity. Finally, chemical modification of proteins present in the initial virus-containing matter may alter their antigenic specificity. This is the primary cause of allergic reactions in humans after booster doses of inactivated rabies vaccine. Despite their inherently low selectivity, ethyleneimine monomer (EI or BEI) have been used as agents for production of the killed antiviral vaccines.

SUMMARY OF THE INVENTION

The invention features a method for inactivating a virus, which method includes treating the virus with an inactivating amount of a composition including an ethyleneimine at a pH less than 7.0 (e.g., a pH between 5.5 and 7.0, or a pH less than 6.8). Preferably, the immunogenicity of the treated virus is enhanced compared to the immungenicity of the same virus treated at a pH greater than or equal to pH 7.0 (e.g., pH 7.5, 8.0, or preferably 7.0). Immunogenicity and inactivation can be measured by methods known in the art, including but not limited to those methods described herein. An ethyleneimine is selected from monomeric and oligomeric forms of ethyleneimine. The concentration of an ethyleneimine is determined by weight/volume (w/v) (e.g, between 0.01% and 1.0% w/v, or between 0.01% and 0.5% w/v). Mixtures of monomeric and oligomeric ethyleneimines, or mixtures of oligomeric ethyleneimines, can be used. Oligomeric includes between 2 and 8 units, e.g., dimeric, trimeric, branched or straight tetrameric, and so on. Examples of viruses include polio, rabies, yellow fever, Japanese encephalitis, tick-borne encephalitis, measles, mumps, Ross River virus, rotavirus, and rubella.

The invention also features a method for inactivating a virus, which method includes contacting the virus with a composition including monomeric ethyleneimine at a pH less than 7.0. The pH will have been determined by a method which includes (a) treating a plurality of samples of the virus with an inactivating amount of a composition containing monomeric ethyleneimine at a plurality of different pH values; (b) measuring in each treated virus sample a characteristic selected from viral inactivation and immunogenicity; and (c) selecting the pH which provides, relative to the other pH values of step (a), a higher viral inactivation or a higher immunogenicity, or a combination thereof.

Other features and advantages of the invention will be apparent from the following description and from the claims.

DESCRIPTION OF THE PREFERRED EMBODIMENTS

The invention features a method of inactivating a virus at a pH less than 7.0 by the action of an electrophilic inactivating agent, e.g., an ethyleneimine (EI). Treatment at an acidic pH inactivates viral nucleic acids with surprisingly less adverse reaction of an electrophilic reagent with viral proteins, when compared with treatment at a pH of 7.0 or higher. Adverse reactions with viral proteins can lead to decreased resistance to proteinases, distintegration of viral particles, alteration of viral antigens, and inhibition of intracellular processing of viral proteins. A virus treated by the disclosed method is therefore likely to be more stable during storage and to have better immunogenicity and antigenic specificity.

Within the pH interval 6.5–8.5, nucleic acid bases remain uncharged. In turn, the nucleophilicity and the rate of modification with electrophilic reagents remain substantially the same. However, alteration of pH affects the nucleophilicity of the amino acid residues having protonizable heteroatoms. For instance, protonation of the imidazole ring in histidine and tryptophan or the hydroxy group of tyrosine almost completely prevents the reaction of the amino acid with an electrophilic reagent.

Other factors make it difficult to predict the effects of a lowered pH on nonspecific reactivity of proteins with EI. Existence of intramolecular interactions among viral proteins and between viral proteins and other components of the medium can significantly alter both accessibility and pKa of these amino acids. Alteration of inactivation conditions may lead to alteration in the higher structure of viral components (both proteins and nucleic acid) and, in turn, affect the rate of the component reactions with EI.

Optimization of inactivation (e.g., minimum time interval for treatment, concentration of EI, ionic strength, temperature, and pH) would decrease the extent of side reactions affecting immunogenic potency and specificity of killed vaccines. Optimal conditions for inactivating viruses for the purpose of preparing a killed viral vaccine include the following: (1) determination of the virus infectivity inactivation rate constants as a function of pH between 6.5 and 8.0 (or between 5.5 and 7.0, or between 5.0 and 7.0); (2) determination of the selectivity of the virus infectivity inactivation (extent of modification of virion proteins and nonviral proteins) at different pH values; and (3) determination of the potency of vaccines inactivated at different pH values.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

Without further elaboration, it is believed that one skilled in the art can, based on the description herein, utilize the present invention to its fullest extent. The following specific examples are, therefore, to be construed merely as illustrative, and not limitative of the remainder of the disclosure in any way whatsoever. Publications mentioned herein are hereby incorporated by reference.

EXAMPLE 1

Determination of the virus infectivity inactivation rate constants as a function of pH between 6.5 and 8.0

The virus inactivation rate constant is used to determine the approximate inactivation conditions required to produce a safe vaccine, as a function of the starting titer of live virus and the extent of inactivation required. Inactivation should generally proceed for a time calculated to give an adequately low titer of viable virus to preclude a meaningful incidence of live virus infection. For many viruses, 12 to 20 logs of inactivation results in a vaccine calculated to deliver less than a single viable virion for every one million vaccine recipients. Indirect methods, such as PCR, used to determine of the extent of virus inactivation by other inactivating agents are misleading, although direct determination of viral infectivity cannot be performed.

Determination of the inactivation rate constant is performed as follows: Freshly distilled ethyleneimine (EI) is dissolved in 0.1M NaCl and 0.1M MOPS buffer or 0.1M Tris HCl buffer for a final concentration of 0.5% (0.125M), 0.1% (0.025M) and 0.02% (0.005M) of EI. The final pH should be 6.5, 7.0, 7.5 or 8.0, respectively. The reagent solution is incubated at 20° C. or 37° C. and added to purified virus suspension (initial titer ~$10^5$–$10^8$ PFU./ml) preincubated in the same buffer, at the same pH, and at the same temperature. Aliquots after incubation of the reaction mixture for 0, 1.0, 2.0, 4.0, 8.0, and 16 hours are removed, the excess of the reagent quenched immediately by addition of 0.1 volume of 1.0M thiosulfate (neutralized to the same pH), incubated at the same temperature for 0.5–1.0 hours, then cooled to 0° C. and kept at this temperature before further dilution with cultural medium and plating. Control—the same reaction mixture without EI. Following inactivation, the virus is titered in the standard fashion used to determine the concentration of replication competent virions remaining. The rate constant of inactivation (k, h-1, mM-1) is calculated as:

$$k = \frac{2.3}{A \cdot t} \log(S_o/S_t)$$

where: $A_3$ final concentration of the reagent in the reaction mixture in mM; $t_3$ time of incubation with the reagent in hours; $S_o$ and $S_{t3}$ titer of the virus before and after t hours of inactivation.

The pH must be precisely measured (±0.05) and kept constant before and during inactivation. The temperature of the reaction mixture must be constant (±1.0° C.). The virus should be preincubated at the given temperature as long as it is necessary to observe the expected exponential (semilogarithmic) kinetics of inactivation. Neither reagent solution nor virus suspension must contain determinable (>1 mM) amounts of phosphate, citrate and other sources of oligoanions. Virus suspension must not contain natural or artificial oligocations (spermine, spermidine, etc.) or other compounds able to change the higher structure of the viral genome or nucleoprotein. Genome lesion repair, recombination of genome at high multiplicity of infection, or reassortment of viral genome containing fragmented genome may lead to non-exponential inactivation kinetics. This may be suspected on the basis of knowledge of the viral genome. It can be observed experimentally and taken into account in further studies.

EXAMPLE 2

Determination of the selectivity of the virus infectivity inactivation at different pH's with regard to virion proteins and nonviral proteins Selectivity is the ratio of the viral genome modification to the rate of modification of other components of the reaction mixture (viral or other proteins, glycoproteins, polysaccharides, etc.). Modification of a single nucleoside residue in the viral genome prevent its complete replication and, hence, reproduction of the virus. On average, appearance of 2.3 modified residues (preventing complete genome replication) per genome leads to a one log decrease in virus infectivity.

The most important adverse reactions may be caused by degradation of virion or by modification of other than genome biopolymers: proteins, glycoproteins and polysaccharides. Degradation of the virion leads to significant (several orders of magnitude) decrease in the immunogenicity that requires proportional increase in the amount of vaccine necessary to elicit the proper immune response. The other and more serious consequences are determined by modification of other (besides genome) components of the reaction mixture, mainly of viral and, in many cases, of other proteins and macromolecules present in the reaction mixture.

Fortunately, each genome contain much more exposed reactive residues (purines in nucleic acids are the main target for electrophilic reagents) than any other molecule. Moreover, only genome is, as a rule, in only a single copy per virion. All other molecules that are presented by many copies (excessive copies of each macromolecule per virion), and, therefore, their modification become visible only when many copies were modified in the same manner during infectivity inactivation. Moreover, the reactivity of nucleic bases in the pH range 6–8 remain essentially the same, while the reactivity of amino acid residues in proteins is changed dramatically in this pH interval and is much lower when being protonated. Hence, the maximum specificity of the genome modification may be obtained by the lowest possible pH that, in the case of EI, is possible at pH about 6.5. In the case of EI ($pK_a$~8.1) this may lead to a small increase in the rate of inactivation, but can decrease significantly the amount of reactive (non-protonated) amino acid residues, and, hence, decrease the rate of their modification relative to inactivation.

Several methods may be used to determine the extent of protein modification, including isoelectric focusing and immunological measurements. In either case, a standard preparation of virus is divided and inactivated at pH's 6.5, 7.0, 7.5, and 8.0 at the appropriate temperature and time to achieve the desired extent of inactivation at each pH. In each case, control preparations of virus are treated identically except for the omission of EI. Following inactivation and quenching with thiosulfate as outlined above, portions of the inactivated and control virus preparations are subjected to isoelectric focusing using standard techniques. Since modification of amino acid residues with EI leads to an increase in the $pK_a$ of the protein, isoelectrofocusing is a sensitive method for detecting protein modification. Protein bands can be detected in the IEF gels by any standard technique such as Coomassie blue staining, silver staining or autoradiography if labelled virus has been used. The results will reveal variability in the extent of alteration of the banding pattern among the different conditions of inactivation, and will allow the choice of the condition resulting in least modification of proteins. If the virus is suspended in protein-containing media during inactivation, modification of the medium protein should also be determined by IEF following removal of the virus from the inactivation mixture by high speed centrifugation.

As an additional test of selectivity of inactivation, the inactivated virus and control preparations may be subjected to immunological assessment by ELISA or a similar standard assay, designed to determine the reactivity of virion proteins with standardized immunological reagents such as a panel of monoclonal antibodies. To perform this assessment, the inactivated and control virus preparations prepared at different pH's are subject to ELISA under defined conditions. Reductions in antigenicity will usually be found under some conditions of inactivation. Under most conditions, these conditions should be similar (and preferably the same) as those determined by IEF to result in enhanced modification of proteins. In some cases, detectable modification of proteins may be found only under conditions leading to inactivation of the virus infectivity (theoretical value) by more than 50 logs. Even in this case mainly a single hit reaction(s) with proteins (monomodified proteins) can be detected, although modification of the virus genome is as high as several hundred nucleoside residues per polynucleotide molecule.

EXAMPLE 3

Determination of the potency of vaccines inactivated at different pH's

Following determination of the extent of modification of proteins, the inactivated virus preparations are tested for vaccine potency. To accomplish this, the virus preparations inactivated at various pH's are administered to the appropriate animal under conditions designed to provide an effective immune response, e.g., three to four administrations with or without an immunological adjuvant at suitable intervals. Ordinarily, each vaccine preparation will be given at various dose levels to allow determination of a dose response relationship, a measure of potency. At baseline and one week following each administration of vaccine, blood or other fluid is tested for antibody against viral components. Following the final vaccine administration, the animal is tested for protective efficacy by administration of wild-type virus and observation for consequences of viral infection. In this way, potency of the vaccine produced under each condition can be evaluated. For some viruses, assessment of either immune response or protective efficacy may be the more valuable parameter for prediction of vaccine effectiveness in humans.

What is claimed is:

1. A method for inactivating a virus selected from the group consisting of polio virus, rabies virus, yellow fever virus, Japanese encephalitis virus, tick-borne encephalitis virus, measles virus, mumps virus, Ross River virus, rotavirus, and rubella, said method comprising treating said virus with an inactivating amount of a composition comprising an ethyleneimine at a pH less than 7.0.

2. The method of claim 1, wherein said pH is between 5.5 and 7.0.

3. The method of claim 1, wherein said pH is less than 6.8.

4. The method of claim 1, wherein the concentration of said ethyleneimine in said composition is between 0.01% and 0.5 % w/v.

5. The method of claim 1, wherein said ethyleneimine is monomeric.

6. The method of claim 1, wherein said ethyleneimine is oligomeric.

7. The method of claim 1, wherein the immunogenicity of the treated virus is enhanced compared to the immunogenicity of the same virus treated at pH 7.0.

8. A method for inactivating a virus selected from the group consisting of poliovirus, rabies virus, yellow fever virus, Japanese encephalitis virus, tick-borne encephalitis virus, measles virus, mumps virus, Ross River virus, rotavirus, and rubella, said method comprising contacting said virus with monomeric ethyleneimine at a pH less than 7.0 which has been determined by (a) treating a plurality of samples of said virus with an inactivating amount of monomeric ethyleneimine at a plurality of different pH values;

(b) measuring in each treated virus sample a characteristic selected from viral inactivation and immunogenicity; and (c) selecting the pH which provides, relative to the other pH values of step (a), a higher viral inactivation or a higher immunogenicity, or a combination thereof.

* * * * *